United States Patent [19]

Kihara et al.

[11] Patent Number: 4,962,200

[45] Date of Patent: Oct. 9, 1990

[54] NITROGEN-CONTAINING COMPOUND

[75] Inventors: Noriaki Kihara, Iwakuni; Ikuo Tomino; Hiroaki Tan, both of Otake; Takafumi Ishihara, Toyonaka, all of Japan

[73] Assignee: Mitsui Petrochemical Industries, Ltd., Tokyo, Japan

[21] Appl. No.: 188,219

[22] Filed: Apr. 29, 1988

[30] Foreign Application Priority Data

Apr. 30, 1987 [JP] Japan .................................. 62-104753

[51] Int. Cl.$^5$ .......................................... C07D 401/06
[52] U.S. Cl. .................................... 544/333; 540/587; 544/51; 544/105; 546/165; 548/181; 548/465
[58] Field of Search ........................ 544/333; 546/165

[56] References Cited

U.S. PATENT DOCUMENTS 4,623,377  11/1986  Kurahashi et al. ................. 546/165

OTHER PUBLICATIONS

Profft, "Chemical Abstracts", vol. 51, 1957, col. 5074a.
Arnol'dova et al., "Chemical Abstracts", vol. 66, 1967, col. 53995x.
Sheinkman et al., "Chemical Abstracts", vol. 70, 1969, col. 19857b.
"Chemical Abstracts", vol. 77, 1972, col. 61985m.

Primary Examiner—Glennon H. Hollrah
Assistant Examiner—James H. Turnipseed
Attorney, Agent, or Firm—Sherman & Shalloway

[57] ABSTRACT

A novel nitrogen-containing compound capable of preventing hardening of blood vessels by controlling formation of peroxide lipids in cell membranes, which is valuable as an anti-arteriosclerotic agent, is disclosed.

19 Claims, No Drawings

NITROGEN-CONTAINING COMPOUND

BACKGROUND OF THE INVENTION (1) Field of the Invention

The present invention relates to a novel nitrogen-containing compound. More particularly, the present invention relates to a novel nitrogen-containing compound having a function of inhibiting formation of a peroxide lipid in a cell membrane.

(2) Description of the Prior Art

The fact that if a lipid of a cell membrane undergoes peroxidation, the formed peroxide lipid participates in pathologic outbreak and development of arteriosclerosis has been clarified, and it has been found that a compound capable of controlling formation of a peroxide lipid is valuable as an anti-arteriosclerotic agent.

For example, Japanese Patent Application Laid-Open Specification No. 165326/86 teaches that a specific isoquinoline derivative or a salt thereof is valuable as an agent for controlling formation of a peroxide lipid. The disclosed isoquinoline derivative or salt exerts a lysosome-releasing action, an action of inhibiting production of active oxygen and/or an action of inhibiting release of histamine in addition to the above-mentioned function of controlling formation of a peroxide lipid. Namely, the isoquinoline derivative or salt is characterized in that it exerts the pharmacological action over a broad range. However, the pharmacological effect of inhibiting formation of a peroxide lipid by the isoquinoline derivative or salt is still insufficient.

SUMMARY OF THE INVENTION

We made investigation with a view to finding a compound having an excellent function of inhibiting formation of a peroxide lipid, and as the result, we found that a specific novel nitrogen-containing compound is especially excellent in the function of inhibiting formation of a peroxide lipid. We have now completed the present invention based on this finding.

More specifically, in accordance with the present invention, there is provided a novel nitrogen-containing compound represented by the following general formula [I] or a pharmacologically acceptable salt thereof:

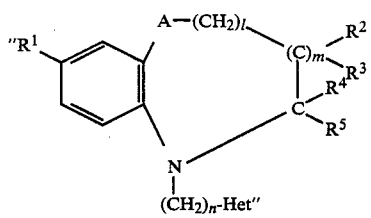

wherein $R^1$ stands for a hydrogen atom, a halogen atom or a lower alkyl group, $R^2$ and $R^3$ independently stand for a hydrocarbon group, $R^4$ and $R^5$ independently stand for a hydrogen atom or a lower alkyl group, with the proviso that $R^2$, $R^3$, $R^4$ and $R^5$ may form a benzene ring with the carbon atoms to which they are bonded, A stands for a methylene group which may be substituted with a lower alkyl group, or an oxygen or sulfur atom, l is 0 or 1, m is 0 or 1, n is an integer of from 1 to 3, and Het is a group represented by one of the following formulae [II] through [X]:

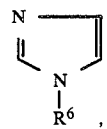

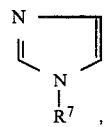

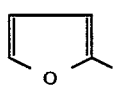

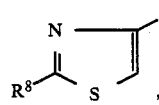

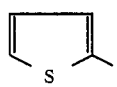

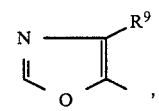

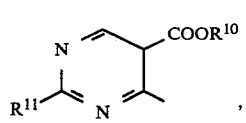

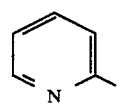

and

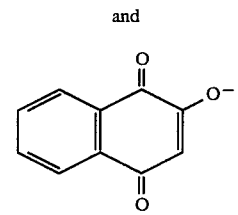

in which $R^6$ stands for a lower alkyl group, $R^7$ stands for a di-lower-alkyl group-substituted carbamoyl group, $R^8$, $R^9$ and $R^{10}$ independently stand for a lower alkyl group and $R^{11}$ stands for a hydrogen atom, a lower alkyl group or a phenyl group, with the proviso that when A is an oxygen or sulfur atom, Het is a group represented by the formula [IV], when n is at least 2, Het is a group represented by the formula [IV] or [X], when m is 1, $R^2$, $R^3$, $R^4$ and $R^5$ form a benzene ring with the carbon atoms to which they are bonded and Het is a group represented by the formula [III], and when $R^1$ stands for a halogen atom or a lower alkyl group, Het is a group represented by the formula [IV].

It is known that if a lipid of a cell membrane undergoes peroxidation, the cell membrane becomes brittle. From recent clinical statistics, case reports, biochemical experimental reports, pathological observation results and animal experiment results, it is presumed that peroxide lipids participate in pathologic outbreak and development of arteriosclerosis.

This presumption is supported by the following facts. Namely, agglutination or adhesion of platelets is promoted by a peroxide lipid, and a lipoprotein having an abnormally low specific gravity, which is produced by transfer of radicals from a lipid peroxide, undergoes the phagocytosis of a macrophage, and formation of foam cells is promoted and cholesterol is accumulated on the artery wall. Furthermore, denaturation of proteins of endothelial cells by a peroxide lipid results in damage or falling of endothelial cells.

Accordingly, it is construed that a compound having a function of controlling formation of a peroxide lipid acts, for example, as an anti-arteriosclerotic agent for controlling hardening of blood vessels.

As the result of research made by us, it was found that a nitrogen-containing compound represented by the above-mentioned general formula [I] or a salt thereof has an excellent action of controlling formation of peroxide lipids, as shown in examples given hereinafter.

DETAILED DESCRIPTION OF THE PREFERRED EMBODIMENTS

The compound of the present invention is represented by the above-mentioned general formula [I]. As the halogen for $R^1$, there can be mentioned chlorine and bromine, and chlorine is preferred. As the lower alkyl group for $R^1$, there can be mentioned a methyl group, an ethyl group and a propyl group, and a methyl group is especially preferred. $R^2$ and $R^3$ independently stand for a hydrocarbon group, and when m, described below, is 1, $R^2$ and $R^3$, together with $R^4$ and $R^5$, described below, form a benzene ring with the carbon atoms to which they are bonded. As the lower alkyl group for $R^4$ and $R^5$, there can be mentioned lower alkyl groups as mentioned above with respect to $R^1$, and it is especially preferred that each of $R^4$ and $R^5$ be a methyl group. As the lower alkyl group as the substituent of the methylene group A, there can be mentioned lower alkyl groups as mentioned above with respect to $R^1$, and a methyl group is especially preferred. Het is a group selected from groups represented by the formulae [II] through [X]. As the lower alkyl group for $R^6$, the lower alkyl group as the substituent of $R^7$ and the lower alkyl group for $R^8$, $R^9$, $R^{10}$ and $R^{11}$, there can be mentioned lower alkyl groups as described above with respect to $R^1$, and a methyl group and an ethyl group are preferred. It is especially preferred that $R^{10}$ be an ethyl group and each of the other lower alkyl groups be a methyl group.

As the pharmacologically acceptable salt of the compound represented by the general formula [I], there can be mentioned salts of acids forming anion containing non toxic acid addition salts, such as a hydrochloric acid salt, a hydrobromic acid salt, a sulfuric acid salt, a hydrogensulfate, a maleic acid salt, a fumaric acid salt, a succinic acid salt, a lactic acid salt, a tartaric acid salt, a benzoic acid salt, a citric acid salt, a gluconic acid salt, a saccharic acid salt, a methane-sulfonic acid salt, a p-toluene-sulfonic acid salt and a naphthalene-sulfonic acid salt, hydrates of these salts, quaternary ammonium and amine salts, and hydrates thereof.

Specific examples of the compound of the general formula [I] according to the present invention are shown in Table 1. Incidentally, in Table 1, Me stands for a methyl group and Et stands for an ethyl group.

TABLE 1

| Compound No. | Structural Formula |
|---|---|
| (1) | |
| (2) | |
| (3) | |
| (4) | |
| (5) | |
| (6) | |
| (7) | |
| (8) | |

TABLE 1-continued

| Compound No. | Structural Formula |
|---|---|
| (9) – (16) | (structural formulas) |
| (17) – (21) | (structural formulas) |

The processes for the preparation of nitrogen-containing compounds represented by the general formula [I] will now be described.

Process A

In the case where Het in the general formula [I] is a group other than

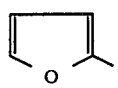 [IV]

and

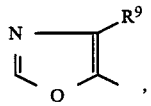 [VII]

the compound [I] is synthesized according to the process A represented by the following reaction formula:

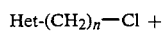 Process A (XIV)

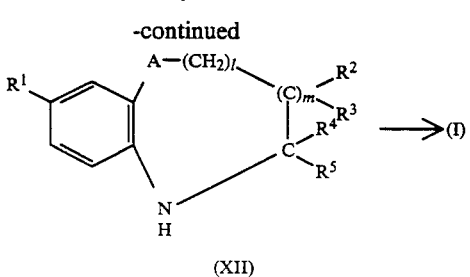

Namely, the compound is obtained by reacting known compounds [XIV] and [XII] in an inert solvent such as toluene or N,N-dimethylformamide (hereinafter referred to as "DMF") at a temperature in the range of from room temperature to 150° C., preferably from 50° to 130° C. The reaction may be carried out in the presence of a base such as triethylamine or pyridine or by using the compound [XII] in excess.

Process B

In the case where Het is a group represented by the formula [IV] or [VII], the compound [I] is synthesized according to the process B represented by the following reaction formula:

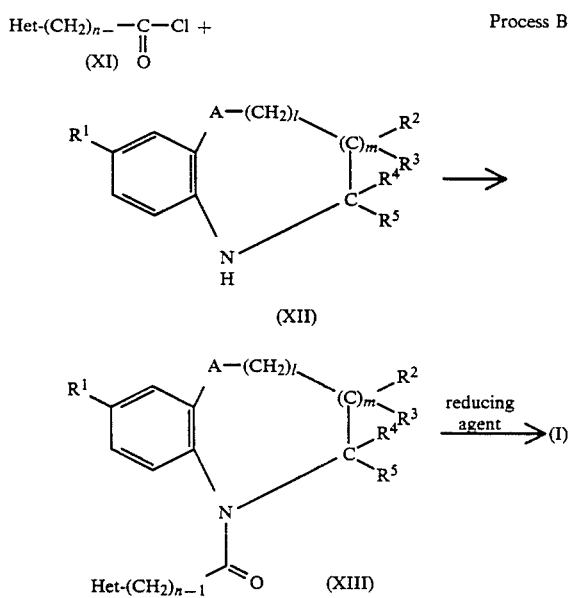

Namely, the compound [XIII] is obtained by reacting known compounds [XI] and [XII] in an inert solvent such as toluene in the presence of a base such as triethylamine or pyridine at a temperature of 0° to 100° C., preferably 0° to 50° C., according to customary procedures, and the compound [I] is obtained by reducing the compound [XIII] in a solvent such as tetrahydrofuran (hereinafter referred to as "THF") at a temperature of 50° to 100° C. by using a reducing agent such as lithium aluminum hydride or diisobutyl aluminum hydride.

The method for administration of the nitrogen-containing compound of the present invention as the agent for controlling formation of a peroxide lipid is not particularly critical. Preferably, as the non-oral administration means, there can be adopted hypodermic injection, intravenous injection, intramuscular injection and intra-abdominal injection, and the nitrogen-containing compound of the present invention can be orally administered in the form of tablets, capsules, powders or elixirs.

A physiological saline solution, a solution of dextrose or a similar saccharide or a glycol such as propylene glycol or polyethylene glycol is preferably used as the liquid carrier. In case of an injection using a physiological saline solution, the concentration of the effective ingredient is adjusted to 0.5 to 20% by weight, preferably 1 to 10% by weight. A suspension or syrup containing 0.5 to 10% by weight of the effective ingredient is preferred as a liquid preparation to be orally administered, and a perfume, a syrup or a pharmaceutical micelle is used as a carrier.

The novel nitrogen-containing compound of the present invention is effective for maintaining the stability in cell membranes and exerts a function of controlling formation of a peroxide lipid. Accordingly, the novel nitrogen-containing compound of the present invention is valuable as an agent for remedy and prevention of diseases caused by formation of peroxide lipids, such as arteriosclerosis.

The present invention will now be described in detail with reference to the following examples that by no means limit the scope of the invention.

EXAMPLE 1

Preparation (process A) of 2-1-(1,2,3,4-tetrahydroquinolyl)methy]pyridine (compound No. 14)

To 0.8 g (4.9 millimoles) of 2-chloromethylpyridine hydrochloride were added 1.3 g (9.8 millimoles) of 1,2,3,4-tetrahydroquinoline, 10 ml of pyridine and 30 ml of toluene, and the mixture was heated and refluxed for 4 hours. Water and ethyl acetate were added to the reaction mixture, and the organic layer was separated, dried with anhydrous sodium sulfate, and concentrated to dryness under reduced pressure. The obtained oil was purified by the silica gel column chromatography (developing solvent: ethyl acetate/hexane=¼) to obtain 0.45 g (the yield was 41%) of intended compound No. 14 in the form of a red oil.

Compounds similarly prepared are shown in Table 2.

EXAMPLE 2

Preparation (process B) of 2-[1-(1,2,3,4-tetrahydroquinolyl)methyl]furan (compound No. 2)

To 1.4 g (10.5 millimoles) of 1,2,3,4-tetrahydroquinoline were added 1.2 g (11.9 millimoles) of triethylamine and 10 ml of toluene, and a solution of 1.5 g (11.5 millimoles) of 2-furoyl chloride in 10 ml of toluene was added dropwise to the mixture at room temperature. The mixture was stirred for 1 hour and water and ethyl acetate were added to the mixture, and the organic layer was separated, dried with anhydrous sodium sulfate, and concentrated to dryness under reduced pressure to obtain a brown solid. The solid was dissolved in 20 ml of THF and the solution was added dropwise to a suspension of 0.5 g (13.2 millimoles) of lithium aluminum hydride in 20 ml of THF at room temperature. The mixture was heated and refluxed for 1 hour, and 1 ml of water and ether were added to the mixture. Then, anhydrous magnesium sulfate was added to the mixture, and the mixture was stirred for 30 minutes. The solid was removed by filtration, and the obtained filtrate was concentrated to dryness under reduced pressure to obtain a light-yellow liquid. The obtained liquid was purified by the silica gel column chromatography (developing solvent: ethyl acetate/hexane=1/15) to obtain 0.5 g (the yield was 23%) of intended compound No. 2 in the form of a light-yellow liquid.

Compounds similarly prepared are shown in Table 2.

EXAMPLE 3

Preparation of 1-(N,N-dimethylcarbamoyl)-4-[1-(1,2,3,4-tetrahydroquinolyl)methyl]imidazole (compound No. 7)

To 0.5 g (3.7 millimoles) of 4-hydroxymethylimidazole hydrochloride was added 2 ml of thionyl chloride, and reaction was carried out at 60° C. for 1 hours. The excess of thionyl chloride was removed by distillation, and 2 ml of DMF and 0.5 g (3.9 millimoles) of quinoline were added to the residue and reaction was carried out at 60° C. for 1 hour. DMF was removed by distillation under reduced pressure, and the residue was washed with chloroform and ethanol to obtain 0.88 g (the yield was 97%) of imidazolylmethyl quinolinium in the form of a light-brown solid. The solid was dissolved in 5 ml of ethanol and 5 mg of platinum oxide was added to the solution, and 0.75 g (19.8 millimoles) of sodium boron hydride was added to the solution at 60° C. The mixture was heated and refluxed for 3 hours, and water was added to the reaction mixture and the mixture was extracted with dichloromethane. The extract was dried with anhydrous sodium sulfate and concentrated under reduced pressure to obtain 0.8 g of a brown oil. The oil was purified by the silica gel column chromatography (developing solvent: ethanol/toluene =$\frac{1}{3}$). Then, 5 mg of platinum oxide was added to the purified oil and reaction was carried out in a hydrogen atmosphere for 5 hours.

The catalyst was removed by filtration, and the filtrate was concentrated under reduced pressure to obtain 0.42 g (the yield was 55%) of 4-(1,2,3,4-tetrahydroquinolylmethyl)-imidazole in the form of a light-brown oil. The oil was dissolved in 10 ml of pyridine and 1 ml (10.8 millimoles) of dimethylcarbamoyl chloride was added to the solution, and reaction was carried out at 80° C. for 2 hours. Pyridine was removed by distillation under reduced pressure, and an aqueous solution of sodium hydrogencarbonate was added to the residue and the mixture was extracted with toluene. The organic layer was dried with anhydrous sodium sulfate and concentrated under reduced pressure, and the concentrate was purified by the silica gel chromatography (developing solvent: ethyl acetate) to obtain 0.31 g (the yield was 30%) of intended compound No. 14 in the form of a light-brown oil.

EXAMPLE 4

Preparation of 1-(N,N-dimethylcarbamoyl)-4-[1-(2,2,4-trimethyl-1,2,3,4-tetrahydroquinolyl)-methyl]imidazole (compound No. 8)

In 10 ml of ethanol was dissolved 2.0 g (11.5 millimoles) of 1,2-dihydro-2,2,4-trimethylquinoline, and 0.4 g of 10% Pd-C was added to the solution and reaction was carried out at 60° C. in a hydrogen atmosphere for 7 hours. The catalyst was removed by filtration and the filtrate was concentrated under reduced pressure to obtain 1.8 g (the yield was 89%) of 2,2,4-trimethyl-1,2,3,4-tetrahydroquinoline in the form of a light-brown oil. To 0.5 g (3.7 millimoles) of 4-hydroxymethylimidazole hydrochloride was added 3 ml of thionyl chloride and reaction was carried out at 50° C. for 2 hours. The excess of thionyl chloride was removed by distillation under reduced pressure. The residue was dissolved in 10 ml of DMF and a solution of 1.1 g (6.3 millimoles) of 2,2,4-trimethyl-1,2,3,4-tetrahydroquinoline in 5 ml of DMF was added to the above solution at 100° C. Reaction was carried out for 1 hour. DMF was removed from the reaction mixture by distillation under reduced pressure. An aqueous solution of sodium hydrogen-carbonate was added to the residue and the mixture was extracted with dichloromethane. The organic layer was dried with anhydrous sodium sulfate and concentrated under reduced pressure to obtain a light-green oil. The oil was purified by the silica gel column chromatography (developing solvent; ethyl acetate) to obtain 0.35 g (the yield was 39%) of 4-[1-(2,2,4-trimethyl-1,2,3,4-tetrahydroquinolyl)methyl]imidazole in the form of a colorless crystal. Reaction was carried out in the same manner as described in Example 3 by using 4-[1-(2,2,4-trimethyl-1,2,3,4-tetrahydroquinolyl)methyl]imidazole to obtain 0.35 g (the yield was 30%) of intended compound No. 8 in the form of a light-brown oil.

EXAMPLE 5

Preparation of 1-(N,N-dimethylcarbamoyl)-4-(10,11-dihydro-5H-dibenzo[b,f]azepin-5-ylmethyl)imidazole (compound No. 9)

Reaction was carried out in the same manner as described in Example 4 except that 10,11-dihydro-5H-dibenzo[b,f]azepine was used instead of 2,2,4-trimethyl-1,2,3,4-tetrahydroquinoline, whereby intended compound No. 9 was obtained in the form of a light-brown oil (the yield was 32%).

EXAMPLE 6

Preparation of 4-(2-furyl)methyl-3,4-dihydro-2H-benzooxazine (compound No. 11)

In 20 ml of ethanol was dissolved 5.0 g (45.8 millimoles) of 2-aminophenol, and 4.8 g (50.0 millimoles) of furfural was added to the solution and the mixture was stirred for 1 hour at room temperature. Then, 2.3 g (60.8 millimoles) of sodium boron hydride was added to the mixture and the mixture was stirred at room temperature for 2 hours, and 2N hydrochloric acid was added to the mixture and ethanol was removed by distillation under reduced pressure. Then, the residue was neutralized with a 5% aqueous solution of sodium hydroxide and extracted with ethyl acetate. The organic layer was dried with sodium sulfate and concentrated under reduced pressure, and the residue was purified by the silica gel column chromatography (developing solvent: ethyl acetate/hexane=3/7) to obtain 5.0 g (the yield was 58%) of 2-(2-furyl)methylaminophenol in the form of a brown oil. The oil was dissolved in 200 ml of an aqueous solution of 2.5 g of sodium hydroxide, and 2.5 ml (30 millimoles) of 1,2-chlorobromoethane was added to the solution and the mixture was heated and refluxed for 5 hours. The reaction mixture was extracted, and the extract was dried with anhydrous sodium sulfate and concentrated under reduced pressure to obtain a brown oil. The oil was purified by the silica gel column chromatography (developing solvent: chloroform/hexane=$\frac{1}{3}$→1/1) to obtain 0.5 g (the yield was 7.5%) of intended compound No. 11 in the form of a light-brown oil.

EXAMPLE 7

Preparation of 4-(2-furyl)methyl-3,4-dihydro-2H-1,4-benzothiazine (compound No. 19)

Reaction was carried out in the same manner as described in Example 6 by using 2-aminothiophenol to obtain intended compound No. 19 in the form of a light-brown oil (the yield was 80%).

EXAMPLE 8

Other compounds of the present invention could be synthesized according to similar procedures as shown in Table 2. The physical properties and synthesis process (A or B) are shown in Table 2 with respect to these compounds as well as the compounds obtained in Examples 1 through 7.

TABLE 2

| Compound No. | Melting Point (hydrochloride) | NMR ($\delta$, $CDCl_3$) | Synthesis Process |
|---|---|---|---|
| 1 | 197~199° C. | 1.92(2H,quin,J=7Hz), 2.78(2H,t,J=7Hz), 3.12(2H,t,J=7Hz), 3.60(3H,s), 3.60(3H,s), 4.36(2H,s), 6.75(2H,t,J=8Hz), 7.00(2H,t,J=8Hz), 6.98(1H,s), 7.44(1H,s), | A |
| 2 | 118~121° C. | 1.98(2H,quin,J=7Hz), 2.78(2H,t,J=7Hz), 3.37(2H,t,J=7Hz), 4.44(2H,s), 6.20~6.3(2H,m), 6.68(2H,t,J=8Hz), 6.9~7.1(2H,m), 7.36(1H,m), | B |
| 3 | 113~115° C. | 2.00(2H,quin,J=7Hz), 2.70(3H,s), 2.80(2H,t,J=7Hz), 3.42(2H,t,J=7Hz), 4.66(2H,s), 6.60(2H,t,J=8Hz), 6.80(1H,s), 6.94(2H,d,J=8Hz), | A |
| 4 | 130~135° C. | 2.74(3H,s), 3.00(2H,t,J=7Hz), 3.44(2H,t,J=7Hz), 4.38(2H,s), 6.52(1H,d,J=8Hz), 6.72(1H,d,J=8Hz), 6.96(1H,m), 7.05(2H,d,J=7Hz), | A |
| 5 | 106~110° C. | 2.00(2H,quin,J=7Hz), 2.80(2H,t,J=7Hz), 3.36(2H,t,J=7Hz), 4.64(2H,s), 6.6~7.3(7H,m), | A |
| 6 | 120~125° C. | 2.9~3.4(4H,m), 4.46(2H,s), 6.5~7.20(7H,m), | A |
| 7 | oil | 2.00(2H,m), 2.79(2H,t,J=7Hz), 3.41(2H,t,J=6Hz), 4.42(2H,s), 6.58(1H,t,J=7Hz), 6.65(1H,d,J=7Hz), 6.96(1H,d,J=7Hz), 7.00(1H,d,J=1.5Hz), 7.00(1H,t,J=7Hz), 7.85(1H,d,J=1.5Hz), | — |
| 8 | oil | 1.23(3H,s), 1.32(3H,s), 1.37(3H,d,J=7Hz), 1.69(1H,d,J=9Hz), 1.83(1H,dd,J=9.4Hz), 3.01(6H,s), 4.20(1H,d,J=18), 4.64(1H,d,J=18Hz), 6.62(1H,t,J=7Hz), 6.49(1H,d,J=7Hz), 6.95(1H,d,J=2Hz), 6.95(1H,d,J=7Hz), 7.51(1H,d,J=7Hz), 7.85(1H,d,J=2Hz), | — |
| 9 | oil | 2.89(6H,s), 3.20(4H,s), 4.98(2H,brs), 6.8~7.3(9H,m), 7.78(1H,d,J=2Hz), | — |
| 10 | 154~156° C. | 2.94(2H,t,J=8Hz), 3.35(2H,t,J=8Hz), 4.42(2H,s), 6.2~6.3(2H,m), 6.5~6.8(2H,m), 7.0(2H,m), 7.30(1H,m), | B |
| 11 | 107~109° C. | 3.32(2H,t,J=4Hz), 4.20(2H,t,J=4Hz), 4.39(2H,s), 6.18(1H,br,d,J=4Hz), 6.28(1H,m), 6.5~6.9(4H,m), 7.32(1H,brs), | — |
| 12 | 111~114° C. | 1.97(2H,m), 2.20(3H,s), 2.75(2H,t,J=6Hz), 3.30(2H,t,J=6Hz), 4.40(2H,s), 6.96(1H,d,J=7Hz), 7.05(1H,t,J=7Hz), 7.71(1H,s), | B |
| 13 | deliquescent | 1.9~2.1(4H,m), 2.6~2.8(4H,m), 3.2~3.4(4H,m), 6.00(1H,m) 6.30(1H,m), 6.4~6.6(2H,m), 6.9~7.1(2H,m), 7.30(1H,m), | B |
| 14 | 135~137° C. | 2.04(2H,quin,J=7Hz), 2.84(2H,t,J=7Hz), 3.45(2H,t,J=7Hz), 4.60(2H,s), 6.42(1H,d,J=8Hz), 6.62(1H,d,J=8Hz), 6.96(2H,t,J=8Hz), 7.24(2H,m), 7.60(1H,m), 8.58(1H,m), | A |
| 15 | deliquescent | 1.39(3H,t,J=8Hz), 2.00(2H,quin,J=7Hz), 2.66(3H,s), 2.82(2H,t,J=7Hz), 3.44(2H,t,J=7Hz), 4.36(2H,q,J=8Hz), 4.86(2H,s), 6.42(1H,t,J=8Hz), 6.60(1H,d,J=8Hz), 6.94(2H,t,J=8Hz), 9.00(1H,s), | A |
| 16 | deliquescent | 1.41(3H,t,J=8Hz), 2.06(2H,quin,J=7Hz), 2.88(2H,t,J=7Hz), 3.54(2H,t,J=7Hz), 4.44(2H,q,J=8Hz), 5.00(2H,s), 6.44(1H,d,J=8Hz), 6.58(1H,d,J=8Hz), 6.87(1H,d,J=8Hz), 7.03(1H,d,J=8Hz), 7.40(3H,m), 8.30(2H,m), 9.21(1H,s), | A |
| 17 | deliquescent | 1.39(3H,t,J=8Hz), 2.00(2H,quin,J=7Hz), 2.66(3H,s), 2.82(2H,t,J=7Hz), 3.44(2H,t,J=7Hz), 4.36(2H,q,J=8Hz), 4.86(2H,s), 6.42(1H,d,J=8Hz), 6.60(1H,d,J=8Hz), 6.94(2H,t,J=8Hz), 9.08(1H,s), 9.12(1H,s), | A |
| 18 | 104~108° C. | 1.98(2H,quin,J=8Hz), 2.76(2H,t,J=7Hz), 3.48(2H,t,J=7Hz), 3.80(2H,t,J=8Hz), 4.18(2H,t,J=8Hz), 6.12(1H,s), 6.5~6.7(2H,m), 6.9~7.2(2H,m), 7.6~7.8(2H,m), 8.0~8.2(2H,m), | A |
| 19 | 95~104° C. decomposition | 3.02(2H,t,J=6Hz), 3.68(2H,t,J=6Hz), 4.46(2H,s), 6.20(1H,br,d,J=4Hz), 6.31(1H,m), 6.65(1H,br,d,J=7Hz), 6.81(1H,br,d,J=7Hz), 6.92(1H,t,J=7Hz), 7.05(1H,d,J=7Hz), 7.39(1H,brs), | — |
| 20 | 132~135° C. | 1.94(2H,quin,J=8Hz), 2.20(3H,s), 2.72(2H,t,J=7Hz), 3.30(2H,t,J=7Hz), 4.38(2H,s), 6.1~6.3(2H,m), 6.60(1H,d,J=8Hz), 6.80(1H,s), 7.32(1H,m), | — |
| 21 | 118~121° C. | 1.94(2H,quin,J=7Hz), 2.72(2H,t,J=7Hz), 3.34(2H,t,J=7Hz), 4.40(2H,s), 6.14(1H,m), 6.30(1H,m), 6.60(1H,d,J=8Hz), 6.92(1H,s), 6.98(1H,d,J=8Hz), 7.36(1H,m), | B |

With respect to the compounds of the present invention, the activity of inhibiting formation of peroxide lipids was tested according to the following procedures.

Male rats of the Wistar system having a body weight of 200 to 250 g were used. The rat brain was extracted by beheading and homogenized by 50 mM phosphate buffer solution (pH 7.4)(PBS), and centrifugal separation was conducted for 15 minutes under 1000 G. The supernatant was frozen at $-30°$ C. and stored, and when the test was carried out, the frozen supernatant was thawed in running water and diluted with PBS so that the volume was trebled, whereby a living body sample was prepared.

Two samples were formed by adding 10 μl of a solution of the test compound (the final concentration was $10^{-4}$ M) to 990 μl of the living body sample. One sample was incubated at 37° C. for 30 minutes and 0.2 ml of a 35% solution of perchloric acid was added to stop the reaction. The other sample was not incubated but the solution of perchloric acid was immediately added to stop the reaction. Both the reaction liquids were subjected to centrifugal separation at 3000 rpm for 15 minutes. With respect to each sample, by using 0.5 ml of the supernatant, the amount of the peroxide lipid was determined according to the TBA assay [Okawa et al., Anal. Biochem., 95. 351 (1979)], and the difference between both the measured values was determined as the amount of malondialdehyde (MDS)(the unit: nmole/mg protein). The peroxide lipid inhibition ratio was calculated from this MDA amount (A) and the control value (B) (the MDA amount obtained when the test compound was not added) according to the following formula:

$$\text{Peroxide lipid inhibition ratio (\%)} = \frac{B - A}{B} \times 100$$

The obtained results are shown in Table 3.

TABLE 3

| Compound No. | Inhibition Ratio (%) | Compound No. | Inhibition Ratio (%) |
|---|---|---|---|
| 1 | 99.0 | 12 | 97.8 |
| 2 | 97.8 | 13 | 90.5 |
| 3 | 88.7 | 14 | 100.0 |
| 4 | 84.6 | 15 | 100.0 |
| 5 | 93.6 | 16 | 100.0 |
| 6 | 95.4 | 17 | 100.0 |
| 7 | 51.0 | 18 | 97.9 |
| 8 | 91.0 | 19 | 80.9 |
| 9 | 94.0 | 20 | 85.1 |
| 10 | 87.0 | 21 | 87.2 |
| 11 | 56.0 | | |

We claim:

1. A nitrogen-containing compound represented by the following formula (I) or a pharmacologically acceptable salt thereof:

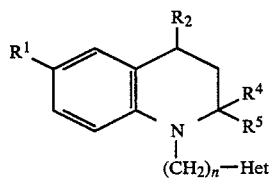

wherein $R^1$ stands for a hydrogen atom, a halogen atom or a lower alkyl group, $R_2$ stands for a hydrogen atom or a methyl group, $R^4$ and $R^5$ independently stand for a hydrogen atom or a lower alkyl group, n is an integer of from 1 to 3, and Het is a group represented by one of the following formula (II) through (X):

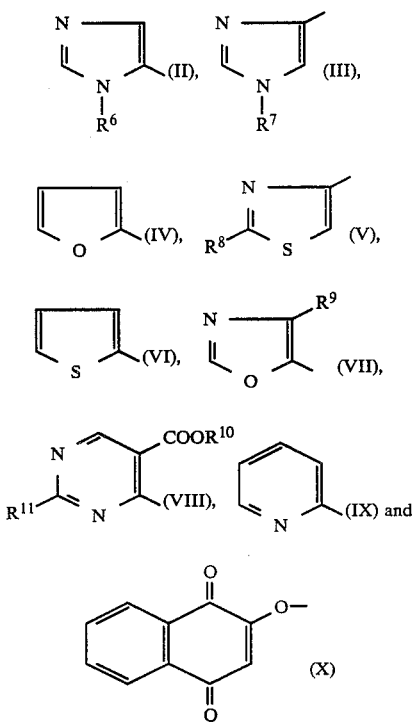

in which $R^6$ stands for a lower alkyl group, $R^7$ stands for a di-lower-alkyl-group-substituted carbamoyl group, $R^8$, $R^9$ and $R^{10}$ independently stand for a lower alkyl group and $R^{11}$ stands for a hydrogen atom, a lower alkyl group or a phenyl group, with the proviso that when n is at least 2, Het is a group represented by formula (IV) or formula (X), and when $R^1$ stands for a halogen atom or a lower alkyl group, Het is a group represented by formula (IV).

2. A nitrogen-containing compound or pharmacologically acceptable salt as set forth in claim 1, which is represented by the following formula:

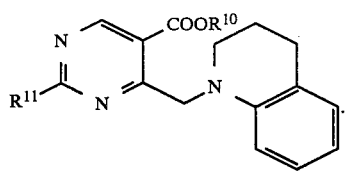

wherein $R^{10}$ and $R^{11}$ are as defined.

3. A nitrogen-containing compound or pharmacologically acceptable salt as set forth in claim 1, which is represented by the following formula:

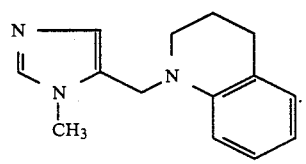

4. A nitrogen-containing compound or pharmacologically acceptable salt as set forth in claim 1, which is represented by the following formula:

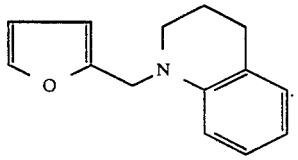

5. A nitrogen-containing compound or pharmacologically acceptable salt as set forth in claim 2, which is represented by the following formula:

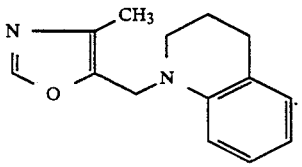

6. A nitrogen-containing compound or pharmacologically acceptable salt as set forth in claim 2, which is represented by the following formula:

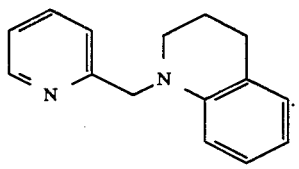

7. A nitrogen-containing compound or pharmacologically acceptable salt as set forth in claim 2, which is represented by the following formula:

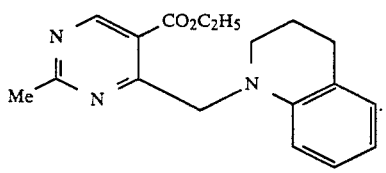

8. A nitrogen-containing compound or pharmacologically acceptable salt as set forth in claim 2, which is represented by the following formula:

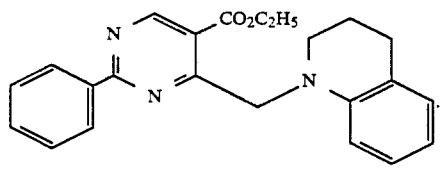

9. A nitrogen-containing compound or pharmacologically acceptable salt as set forth in claim 2, which is represented by the following formula:

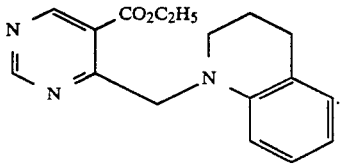

10. A nitrogen-containing compound or pharmacologically acceptable salt as set forth in claim 1, which is represented by the following formula:

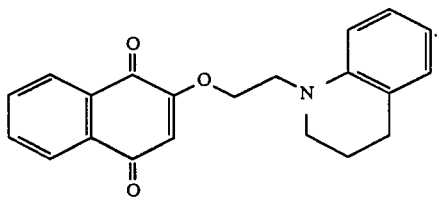

11. A nitrogen-containing compound or pharmacologically acceptable salt as set forth in claim 1, which is represented by the following formula:

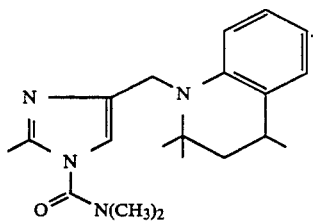

12. A nitrogen containing compound or pharmacologically acceptable salt thereof as set forth in claim 1 which is represented by the formula:

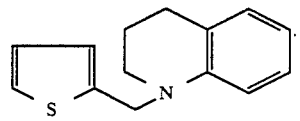

13. A nitrogen-containing compound or pharmacologically acceptable salt thereof as set forth in claim 1 which is represented by the formula:

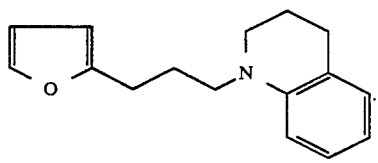

14. The nitrogen-containing compound of claim 1 wherein $R^1$ stand for a hydrogen atom, chlorine atom, a bromine atom, a methyl group, an ethyl group or a propyl group, $R^4$ and $R^5$ independently stand for a hydrogen atom or a methyl group, an ethyl group or a propyl group, $R^6$ stands for a methyl group, an ethyl group or a propyl group, $R^7$ stands for a di-methyl, di-ethyl or di-propyl group-substituted carbamoyl group, $R^8$, $R^9$ and $R^{10}$ independently stand for a methyl group, ethyl group or propyl group, and $R^{11}$ stands for a hydrogen atom, a methyl group, an ethyl group, a propyl group, or a phenyl group.

15. The nitrogen-containing compound of claim 1, wherein $R^1$ is a hydrogen atom, a chlorine atom or a methyl group, $R^4$ and $R^5$ independently stand for a hydrogen atom or a methyl group, $R^6$ stands for a methyl group, $R^7$ stands for a dimethyl-substituted carbamoyl group, $R^8$ and $R^9$ each stand for a methyl group, $R^{10}$ stands for an ethyl group, and $R^{11}$ stands for a hydrogen atom, a methyl group or a phenyl group.

16. The nitrogen-containing compound of claim 1 wherein n is 1.

17. The nitrogen-containing compound of claim 1, wherein n is 2 or 3.

18. The nitrogen-containing compound of claim 1, in the form of its pharmacologically acceptable salt.

19. The nitrogen-containing compound of claim 1, wherein the pharmacologically acceptable salt is a nontoxic acid addition salt selected from the group consisting of hydrochloric acid salt, hydrobromic acid salt, sulfuric acid salt, hydrogensulfate, maleic acid salt, fumaric acid salt, succinic acid salt, lactic acid salt, tartaric acid salt, benzoic acid salt, citric acid salt, gluconic acid salt, saccharic acid salt, methane-sulfonic acid salt, p-toluene-sulfonic acid salt, and a naphthalene-sulfonic acid salt, or a hydrate of these salts.

* * * * *